United States Patent [19]

Takeuchi et al.

[11] Patent Number: 4,941,478
[45] Date of Patent: Jul. 17, 1990

[54] PILLOW FOR CONTROLLING SNORING

[75] Inventors: Shohei Takeuchi; Kuniaki Miyazawa, both of Tokyo; Takenosuke Ikematsu, Noda, all of Japan

[73] Assignee: Shohei Takeuchi, Tokyo, Japan

[21] Appl. No.: 211,303

[22] Filed: Jun. 24, 1988

[30] Foreign Application Priority Data

Feb. 19, 1986 [JP] Japan .................................. 61-34827

[51] Int. Cl.⁵ .............................................. A61F 5/56
[52] U.S. Cl. ........................................ 128/848; 5/437; 5/440
[58] Field of Search ................... 128/848; 5/434, 490, 5/491, 492, 508, 509, 436, 437, 440

[56] References Cited

U.S. PATENT DOCUMENTS

| | | | |
|---|---|---|---|
| 3,998,209 | 12/1976 | Macvaugh | 128/848 |
| 4,220,142 | 9/1980 | Rosen et al. | 128/848 |
| 4,536,905 | 8/1985 | Desantis | 5/436 X |
| 4,748,702 | 6/1988 | Sandler | 128/848 X |

FOREIGN PATENT DOCUMENTS

| | | |
|---|---|---|
| 55-1056 | 1/1980 | Japan . |
| 61-27054 | 6/1986 | Japan . |
| 61-164554 | 7/1986 | Japan . |
| 61-203013 | 12/1986 | Japan . |

Primary Examiner—Robert A. Hafer
Assistant Examiner—Kevin G. Rooney
Attorney, Agent, or Firm—Jeffers, Hoffman & Niewyk

[57] ABSTRACT

A pillow provided with a power unit for rotating its top surface about a horizontal center line of rotation into a new angular position whenever a snoring noise is detected. The angular position of the head of the sleeping person is thereby changed gradually enough not to wake him up but since his larynx is changed into a new state every time the top surface of the pillow is rotated into a new angular position the snoring noise is eventually controlled. Reliable detection of snoring noise is made possible by taking advantage of the periodic nature of the snoring noise.

15 Claims, 7 Drawing Sheets

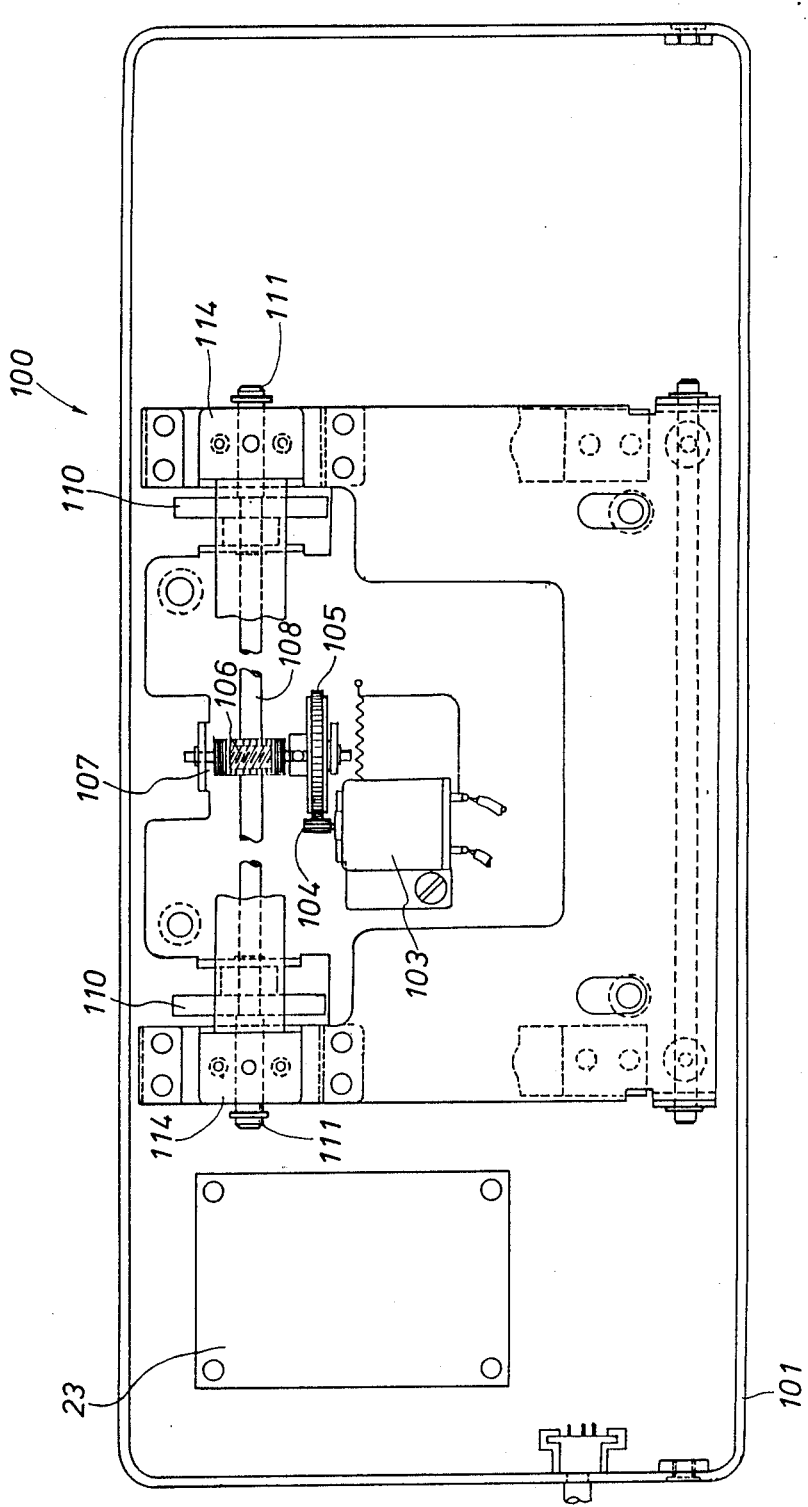

PILLOW FOR CONTROLLING SNORING

The present invention relates to a power driven pillow which is capable of controlling the snoring of a person by a slight rotating motion of its top surface about a substantially horizontal center line of rotation.

BACKGROUND OF THE INVENTION

The snoring has been a major nuisance from the past and there have been a number of proposals which were claimed to be effective in suppressing it. Snoring is caused by the vibration of the palatine uvula and other parts of the larynx of a person as he inhales in sleep. Some people have certain larynx structures which are prone to snoring for pathological and other reasons. In any case, when a person is sleeping, the soft palatine uvula and other parts tend to hang in such a manner that the flow of inhaled air is partly obstructed and the snoring noise is produced as a vibration of the wall of the larynx.

According to the apparatus for preventing snoring proposed in Japanese patent publication No. 55-1056 (which is based on U.S. patent application No. 641,226 filed Dec. 16, 1975), penalizing stimulation is applied to a snoring person. This may prevent the snoring, but the person is prevented from obtaining sleep and causes a considerable discomfort to the snoring person.

Japanese patent laid open publication No. 61-164554 discloses a pillow which is designed to vibrate when any snoring is detected. This also applies stimulation to the snoring person and stimulation of an uncomfortable level must be applied to the snoring person for this vibrating pillow to be effective.

Japanese patent publication No. 61-27054 discloses a bed having a floor board which is hinged at one of its edges so as to be able to slightly twist the upper body of the person sleeping in the bed sideways. When snoring is detected, the floor board is lifted by one step. The floor board is lifted higher by increments as long as the snoring continues. If the snoring ceases for a certain time interval, for instance three minutes, the floor board is lowered by one step. If the snoring has completely stopped, the floor board is lowered by increments until the floor board returns to its initial horizontal position.

Japanese utility model publication No. 61-203013 discloses a pillow having a plate which is hinged at one of its edges and adapted to twist the head of the sleeping person sideways. The plate pushes the head of the sleeping person when a snoring noise is detected, but this pillow is provided with a timer which restores the plate to its initial horizontal position after elapsing of a certain time interval.

These proposals are not satisfactory because they cause substantial stimulation to the sleeping person and the snoring of the person is suppressed at the expense of the sleep or the comfort of the snoring person. Further, in these conventional devices for controlling the snoring of a sleeping person, accurate detection of snoring is not possible because the detection is based on the sound level of the snoring, and other noises could erroneously activate the device to the considerable discomfort to the innocent person who may be sleeping without snoring.

BRIEF SUMMARY OF THE INVENTION

In view of such problems of the prior art, a primary object of the present invention is to provide a device which is effective in suppressing the snoring of a sleeping person without arousing or causing any discomfort to him.

A second object of the present invention is to provide a device which is effective in controlling the snoring of a sleeping person and is simple to use.

A third object of the present invention is to provide a device for controlling the snoring of a sleeping person which is reliable by being free from erroneous activation.

A fourth object of the present invention is to provide a device for controlling the snoring of a sleeping person which is capable of quiet operation.

According to the present invention, these and other objects of the present invention can be accomplished by providing a pillow for controlling snoring of a sleeping person, comprising: a stationary base; a cover placed above the stationary base for placing a head of a person thereon, the cover being disposed in a freely rotatable manner relative to the base about a substantially horizontal central line of rotation; power drive means for causing a rotational motion of the cover about the central line of rotation; snoring noise detecting means for detecting an occurrence of snoring noise; and control means for activating the power drive means so as to move the cover into a different angular position.

Thus, the head of the sleeping person is turned by a certain angle (this angle may be a small angle of a few degrees or a fairly large angle which covers more than a full stroke of the rotating motion of the cover), and the state of his larynx changes accordingly with the result that the snoring eventually stops. This is continued as long as the snoring continues. Once the snoring has stopped, the pillow will stay stationary from then on. In this way, the snoring of the sleeping person can be stopped without waking him up or otherwise causing any discomfort to him. The central line of rotation of the cover may extend either laterally or, in other words, perpendicularly to the spine of the sleeping person, or longitudinally or, in other words, in parallel with the spine of the sleeping person.

It is essential for a device of this kind to be able to accurately detect snoring. To accomplish this, according to a certain aspect of the present invention, the snoring noise detecting means comprises means for detecting a first occurrence of the snoring noise, means for detecting a first quiet period immediately subsequent to the first occurrence of the snoring noise, and means for detecting the second occurrence of the snoring noise immediately subsequent to the first quiet period. Optionally, the snoring noise detecting means may further comprise means for detecting a second quiet period immediately subsequent to the second occurrence of the snoring noise for additional accuracy.

According to one of the basic principles of the present invention, it is desirable for the cover to change its angular position every time the motor is driven. This can be accomplished in a number of ways, but can be conveniently accomplished by driving the power means for a fixed time interval each time because the cover will change its angular position unless the time interval exactly coincides with an exact fraction a full period of the rotating motion of the cover.

At night, even the noise from the power drive means may annoy a person sleeping in the same room. However, if the power means is activated coincidentally as a period of a high snoring noise level, this potential source of additional noise would not cause any problem.

According to a certain theory, some stimulation is desirable for controlling the snoring of a sleeping person. This can be accomplished by causing intermittent changes in the speed of the motion of the cover. This can be conveniently implemented by transmitting the output of the power drive means to the cover by way of a cam and cam follower mechanism, and providing at least in one of contact surfaces of the cam and the cam follower with an irregular contact surface.

BRIEF DESCRIPTION OF THE DRAWINGS

Now the present invention is described in the following with reference to the appended drawings, in which:

FIG. 8 is a plan view of a second embodiment of the pillow for controlling snoring according to the present invention with its covered removed for showing the details of its internal structure.

DETAILED DESCRIPTION OF THE PREFERRED EMBODIMENTS

Figure 1:
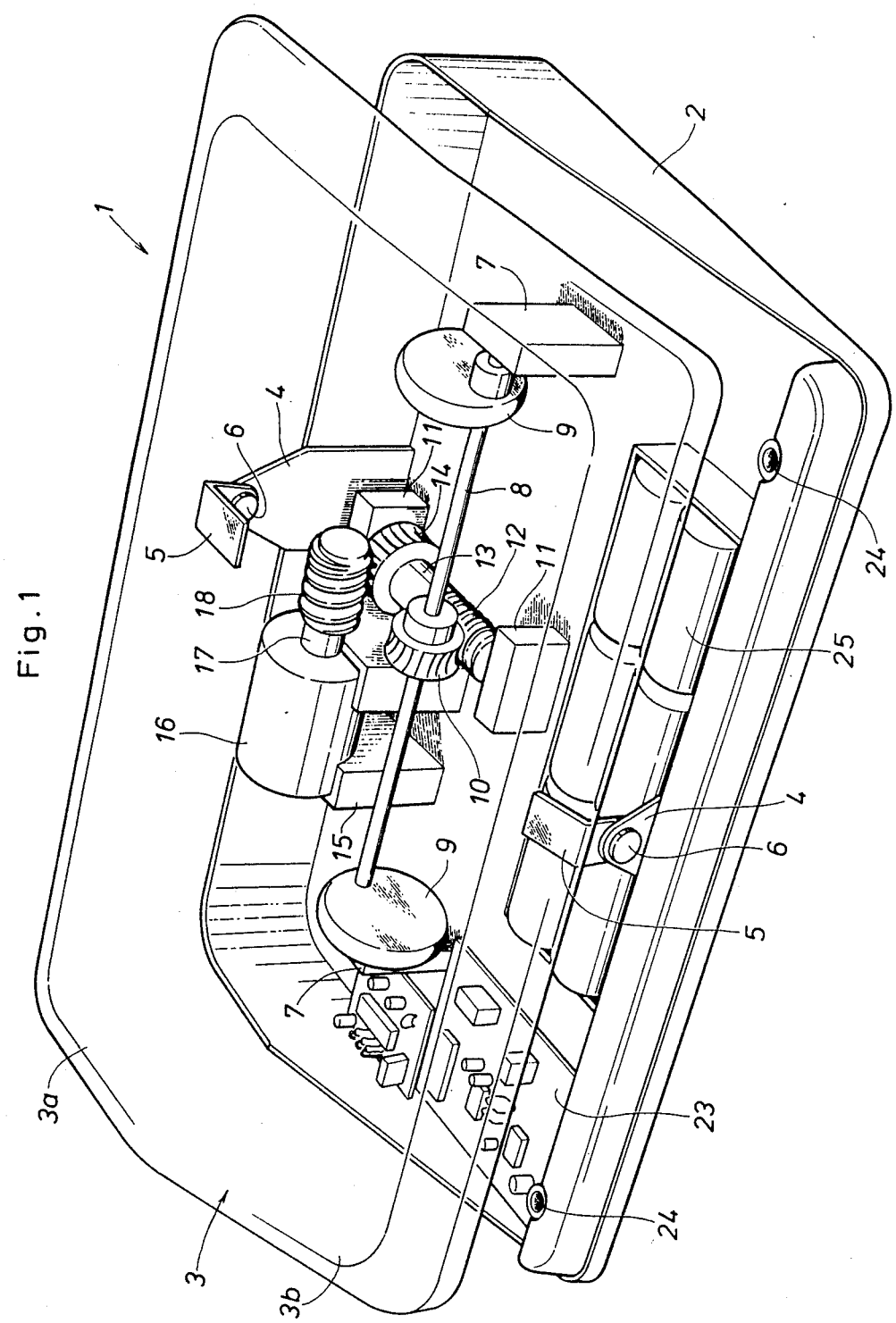
FIG. 1 is a perspective, see-through view of a preferred embodiment of the pillow for controlling snoring according to the present invention.

The pillow 1 for controlling snoring shown in FIG. 1 comprises a casing 2 consisting of a box having an open top made of synthetic resin material, a pair of first brackets 4 integrally attached at either end of a laterally middle part of the casing 1, a pair of second brackets 5 which are pivotally connected to the first brackets 4 by way of pivot pins 6 extending along a lateral central line of the pillow 1, and a cover 3 attached to the second brackets 5. Thus, the cover 3 can rotate about the central line of rotation which passes through the two pivot pins 6. The cover 3 is provided with a relatively horizontal and flat rear part 3a and a downwardly inclined front part 3b so as to present a very low profile to the person who is about to lay his head from the front end of the pillow 1. The assembly including the casing 2 and the cover 3 are covered with a layer of suitable padding material 19 (FIG. 2) and the pillow 1 shown in FIG. 1 is no different from any ordinary pillow as far as its external appearance is concerned.

A pair of blocks 7 are integrally provided in the internal bottom surface of the casing on either side of the central line in a symmetrical arrangement. These blocks 7 rotatable support a lateral shaft 8 which extends laterally or perpendicularly to the central line of the casing 1. This lateral shaft 8 carries a pair of circular eccentric cams 9 adjacent to the blocks 7. A worm gear 10 is fixed mounted in a middle part of the shaft 8 and meshes with a worm 11 which is fixedly attached to a shaft 13. This shaft 13 is in turn supported by a pair of blocks 11 integrally formed in the internal bottom surface of the casing 1 (in the same way as the blocks 7) and extends in parallel with the central line. Further, this shaft 13 fixedly carries a worm gear 14 which meshes with a worm 18 integrally attached to an output shaft 17 of an electric motor 16 supported by a pair of blocks 15 which are also integrally formed in the internal bottom surface of the casing 1. Here, it is understood that the spine of the person who lays his head on this pillow 1 extends substantially in parallel with the central line of rotation passing through the two pivot pins 6.

Figure 2:
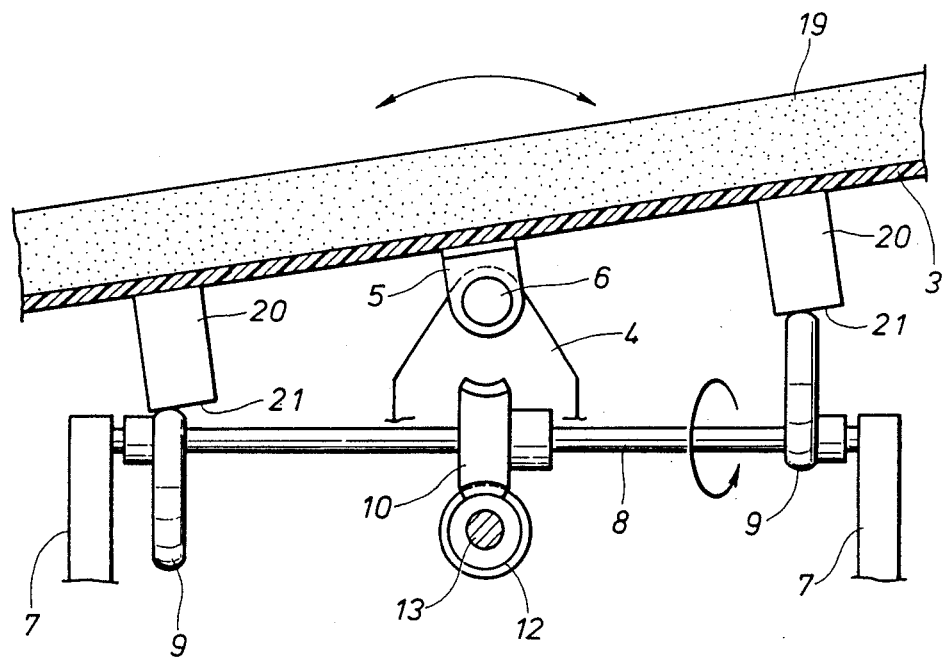
FIG. 2 is a sectional view of a part of the embodiment shown in FIG. 1.

As best shown in FIG. 2, the internal surface of the cover 3 is provided with a pair of blocks 20 having contact surfaces 21 which are in contact with the eccentric cams 9. Since the eccentric cams 9 are 180 degrees out of phase with each other, as the motor 16 is driven, the rotation of the output shaft 13 of the motor 16 which is transmitted to the lateral shaft 8 and the cams 9 causes the cover 3 to rotate about the pins 6 or the central line of rotation of the cover 3.

Figure 3:
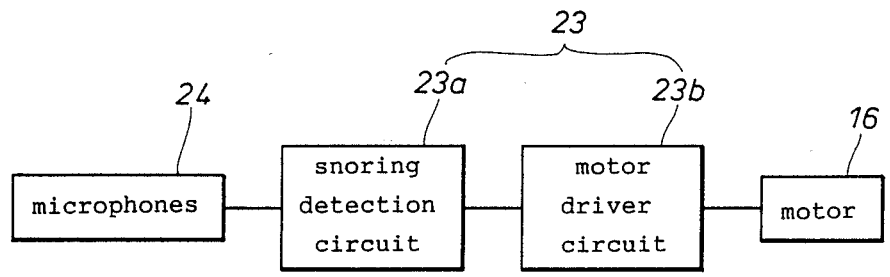
FIG. 3 is a block diagram of the control system of the embodiment shown in FIG. 1.

The casing 1 additionally accommodates therein circuit boards 23 which include a snoring detection circuit 23a and a motor driver circuit 23b (FIG. 3), a pair of microphones 24, located on either side of the casing 24, which are connected to the snoring detection circuit 23a for picking up the snoring noise, and batteries 25 for supplying electric power to the motor 16 and the circuitry included in the circuit boards 23.

Figure 4:
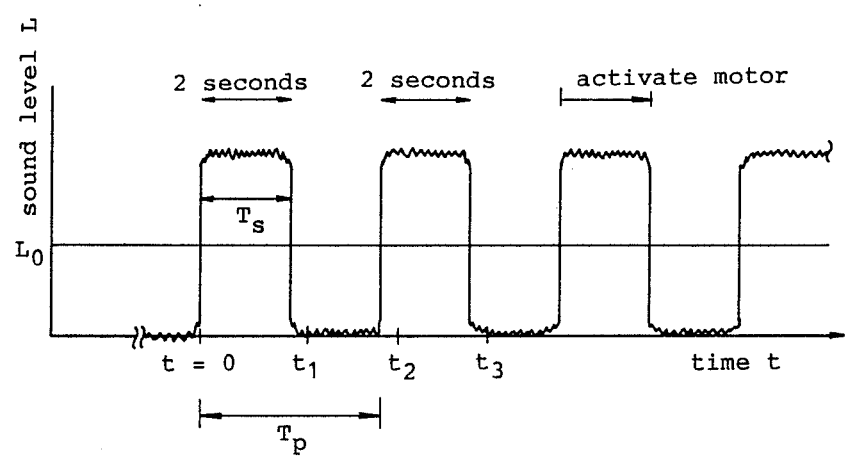
FIGS. 4 and 5 are a wave form diagram and a flow chart, respectively, for describing the operation of the control system shown in FIG. 3.

FIG. 4 shows a typical pattern of the noise level of snoring. Since the snoring occurs as the sleeping person inhales, the snoring noise occurs in an intermittent pattern having a certain regular period, typically 4 seconds $(=T_p)$. The interval of a high snoring noise level $(=T_s)$ typically lasts 2 seconds. In other words, snoring noise occurs at the rate of 15 times per minute for a normal healthy person and the duty ratio is approximately 50%. Obviously, the frequency and the period of the snoring vary from one person to another and depending on the condition of each particular person. Therefore, the above mentioned figures were given only as an example and should not be considered in any way as limiting the scope of the present invention.

Figure 5:
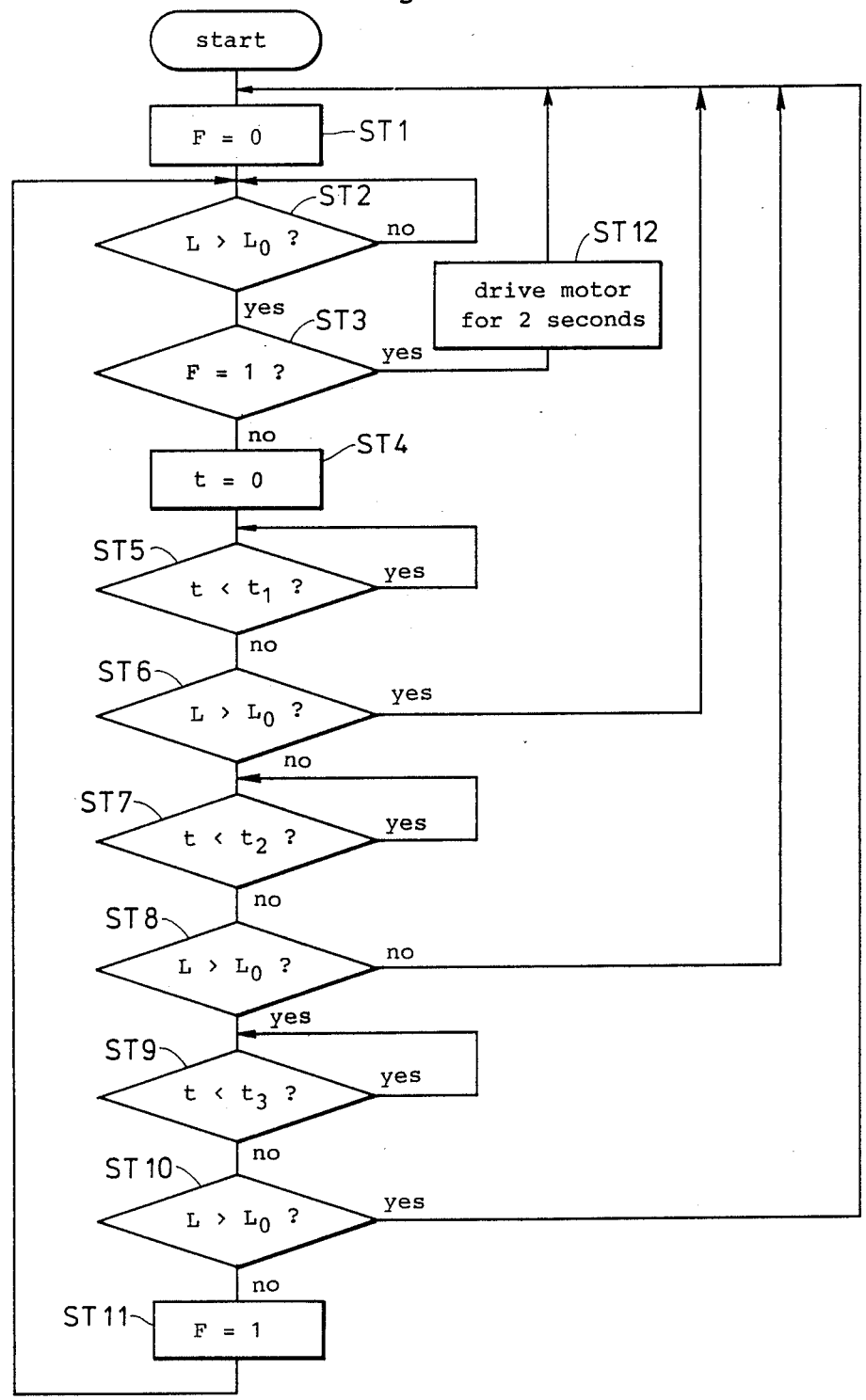

FIG. 5 shows the operation of the snoring detection circuit 23a which can accurately distinguish a snoring noise from other noises.

At first, a flag F is set to zero in ST1 and it is determined whether the noise level L detected by the microphones 24 is greater than a certain threshold level $L_0$ or not in ST2. If the noise level L is less than $L_0$, this process is repeated to continue the monitoring of the noise level detected by the microphones. When the noise level L has exceeded $L_0$, provided that the flag F is still 0 (ST3), the time t is set to zero in ST4. In ST5, the time t is compared with a value $t_1$ and the system flow goes into a loop until the time t exceeds the value $t_1$. The value $t_1$ corresponds to a time interval which is greater than a typical duty time $T_s$ of a snoring noise but less than the full period $T_p$. It is again compared in ST6 whether the noise level L detected by the microphones 24 is greater than the threshold level $L_0$ or not. If the sound level is great, it means that the microphones 24 have detected a certain continuous noise which is not likely to be a snoring noise and the system flow returns to ST1 to start the monitoring of the noise level all over again. If the noise level L has dropped below the threshold level $L_0$, the system flow advances to ST7 and stays there until the time t reaches $t_2$ which corresponds to a time interval slightly greater than the full period $T_p$ of the snoring noise but less than $T_p+T_s$. If the noise level L is still below the threshold level $L_0$, it means that there was only a short burst of noise at t=0 and has ceased since. Therefore, the system flow return to ST1 and the monitoring of the noise level is started all over again. If the noise level L is again higher than the threshold level in ST8, it means that a regular, periodic noise, which is very likely to be a snoring noise, has been detected and the motor, therefore, should be driven to rotate the cover 3 of the pillow 1 over a certain angle.

However, according to the present embodiment, to the end of coinciding the operation of the motor 16 with the duty period of the snoring and thereby masking the noise from the motor with the snoring noise, the following steps are taken. After the elapsing of the time $t_3$ which is later than the end of the second duty period but earlier than the beginning of the third duty period (ST9), the noise level L is compared with the threshold level $L_0$ in ST10 to increase the probability of accurately detecting an actual snoring noise and the flag F is set to 1 in ST11. Then, the system flow returns to ST2. The noise level L is compared with the threshold level $L_0$ in ST2 to detect the beginning of the third duty period. When it is detected, since the flag F was set to 1 in ST11, the system flow advances from ST3 to ST12 where the motor 16 is driven for two seconds which correspond to a typical duty period $T_s$ of a snoring noise or which may be slightly less than that. After the motor 16 has been driven for two seconds, the system flow returns to ST1 and the monitoring of the noise level is resumed all over again.

Since the inclination angle of the cover 3 after the operation of the motor for two seconds is generally different from the original inclination angle, the state in the larynx of the sleeping person changes and there is a high probability that the snoring ceases. If the snoring ceases, the inclination angle of the cover 3 of the pillow will remain the same. If the snoring did not cease, then the previously mentioned process is repeated for accurate detection of the snoring noise and the motor 16 is eventually driven again for two seconds. Thus, the inclination angle of the cover 3 changes into yet another different angle. In doing so, the inclination angle of the cover 3 of the pillow 1 is sequentially changed until it eventually takes a value which is effective in preventing the occurrence of the snoring noise.

Figure 6:
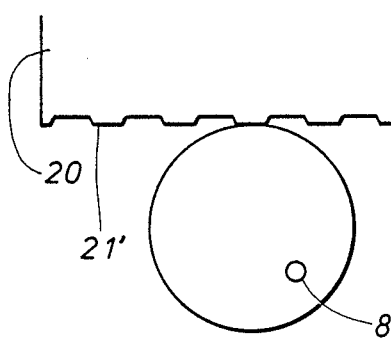
FIG. 6 is a local sectional view of a modified embodiment of a part of the drive mechanism of the pillow according to the present invention.

FIG. 6 shows an alternate embodiment of the contact surfaces 21' of the cover 3 which cooperate with the eccentric cams 9. In this embodiment, the contact surfaces 21' are provided with a certain irregularity. Since the contact points of the eccentric cams 9 change as they rotate, the irregularity of the contact surfaces 21' causes a slight speed fluctuation in the rotating motion of the cover 3. This irregular motion of the cover 3 produces a certain stimulating effect and could substantially improve the effect of the pillow in controlling the snoring of the sleeping person.

Figure 7:
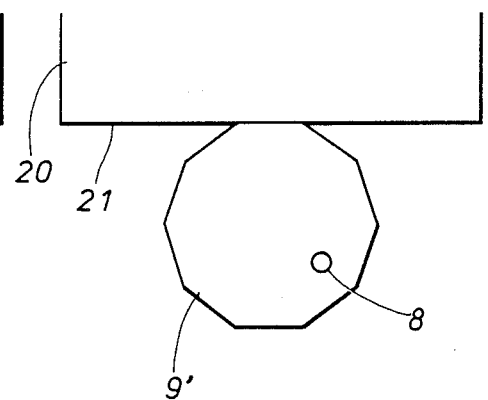
FIG. 7 is a local sectional view of another modified embodiment of a part of the drive mechanism of the pillow according to the present invention.

FIG. 7 shows an alternate embodiment of the eccentric cams 9' which are provided with slight irregular cam profiles which produce the substantially same effect as the irregular contact surfaces 21' shown in FIG. 6.

Figure 9:
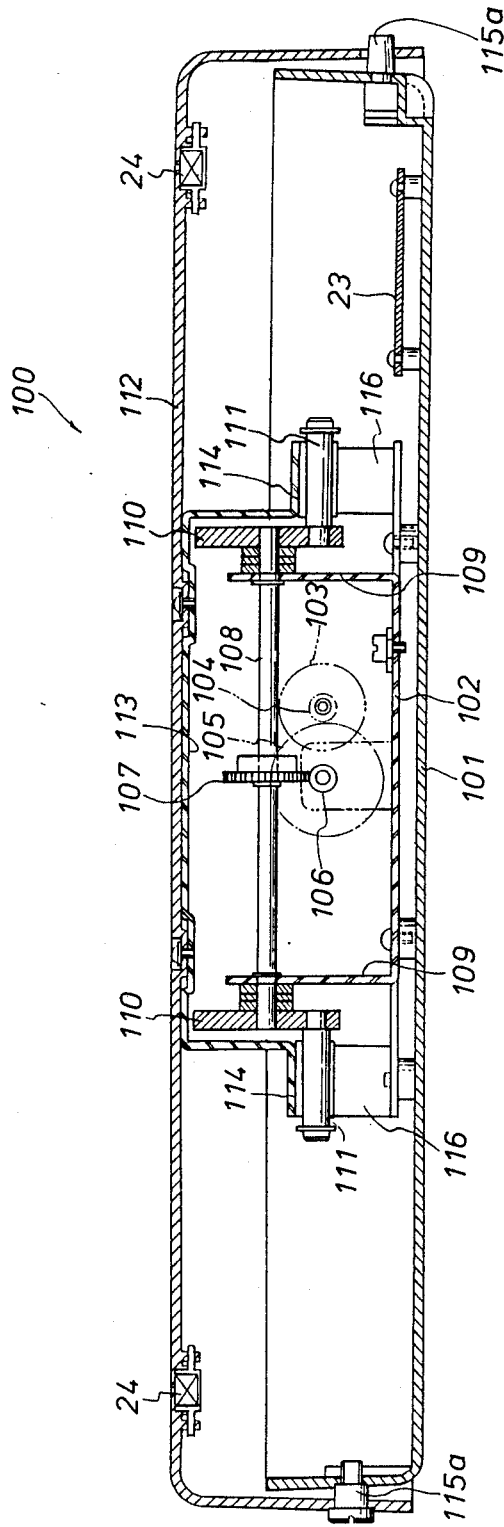
FIGS. 9 and 10 are a sectional front and a side view of the embodiment shown in FIG. 8.
Figure 10:
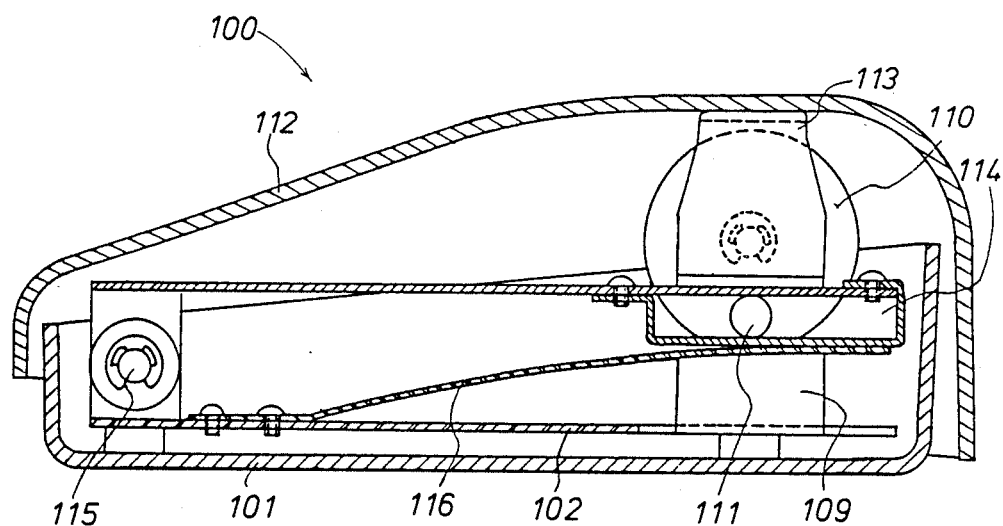

FIGS. 8, 9 and 10 show a second embodiment of the present invention. This embodiment comprises a casing 101 consisting of a box having an open top, a cover 112 which substantially covers the casing 101 in the same manner as the cover 3 of the first embodiment, and an internal floor panel 102 on which are mounted a motor 103, a pinion gear 104 attached to an output shaft of this motor 103, a spur gear 105 meshing with the pinion gear 104, a worm 106 fixedly attached to a rotary shaft common to the spur gear 105, and a worm gear 107 meshing with the worm 106. The worm gear 107 is fixedly attached to a shaft 108 which extends laterally and is rotatably supported by a pair of upright brackets 109 which are bent from the floor panel 102. The two lateral ends of this shaft 108 extending beyond the brackets 109 are each provided with a wheel 110 integrally attached thereto and each of the wheels 110 is provided with a laterally projecting eccentric pin 111. These pins 111 are received in pin holders 114 which depend from the cover 112 by way of a bracket 113. The pin holders 114 each define a slot extending horizontally and perpendicularly relative to the lateral shaft 108. The bracket 113 attached to the cover 112 is hinged to the floor panel 102 by way of a pivot shaft 115 extending laterally adjacent to the lower end of the pillow 100 as seen in FIG. 8 or, in other words, adjacent to the neck of the person who is laying his head on this pillow 100. The cover 112 and the casing 101 are pivotally attached to each other by a pair of pivot pins 115a which align with the pivot shaft 115. Further, the cover 112 is normally biased upward by means of a pair of sheet springs 116 which, mounted in the lower brackets 9 and pressed against the lower surfaces of the pin holders 114. This pillow 100 is also covered by a layer of padding material not shown in the drawings and is very similar to a common pillow in external appearance.

Thus, according to this embodiment, the cover 112 rotates or inclines in the fore and aft direction about the pivot shaft 115 as the pins 111 move inside the corresponding pin holders 114. In this embodiment also, when a snoring noise is detected, the cover 112 rotates into a different angular position each time and sequentially adjusts the state of the larynx of the person who is laying his head on this pillow until the snoring stops.

According to the present invention, the rotating motion of the cover is gradual and would not cause excessive stimulation to the sleeping person. Therefore, the snoring can be effectively controlled without waking up or causing any discomfort to the snoring person.

Although the present invention has been shown and described with reference to the preferred embodiments thereof, it should not be considered as limited thereby. Various possible modifications and alterations could be conceived of by one skilled in the art to any particular embodiment, without departing from the spirit of the invention. For instance, the cover 3 may be provided with a depression for accommodating therein cooling substances such as ice cubes for providing added comfort to the person who lays his head on this pillow. Further, it is possible to change the angular position of the cover 3 not only by activating the motor for a fixed time interval but also by activating the motor for a random time interval every time a snoring noise is detected. Alternatively, it is possible to program the motor driver circuit 23b so as to change the angular position of the cover every time a snoring noise is detected according to a predetermined schedule.

What we claim is:
1. A pillow for controlling snoring of a sleeping person, comprising:
   a stationary base;
   a cover placed above the stationary base for placing a head of a person thereon, the cover being disposed in a freely rotatable manner relative to the base about a substantially horizontal central line of rotation;

power drive means mounted on said stationary base for causing a reciprocating rotational motion of the cover about the central line of rotation;

snoring noise detecting means for detecting an occurrence of snoring noise; and control means operatively connected to both the power drive means and the snoring noise detecting means for activating the power drive means for a predetermined time interval upon detection of snoring by said snoring noise detecting means whereby said cover is rotated into a different angular position.

2. A pillow as defined in claim 1, wherein the central line of rotation extends laterally with respect to said base.

3. A pillow as defined in claim 1, wherein the central line of rotation extends longitudinally with respect to said base.

4. A pillow as defined in claim 1, wherein the power means is activated during a time interval when a snoring noise level in excess of a predetermined threshold level is detected by the snoring noise detecting means.

5. A pillow as defined in claim 1, further comprising means for causing intermittent changes in the speed of the motion of the cover.

6. A pillow as defined in claim 5, wherein the powered drive means is functionally connected to the cover by way of a cam and cam follower mechanism, and the means for causing intermittent changes in the speed of the motion of the cover comprises an irregular contact surface provided on at least one of the contact surfaces of the cam and the cam follower.

7. A pillow as defined in claim 1, wherein the snoring control means activates the power drive means upon detection by the snoring noise detecting means of a sequence of snoring noises consisting of a snoring noise at a noise level higher than a first predetermined threshold level and of a time duration within a first predetermined time range, immediately followed by a snoring noise at a noise level lower than a second predetermined threshold level and of a time duration within a second predetermined time range, and then immediately followed by a snoring noise at a noise level higher than said first predetermined threshold level.

8. A pillow as defined in claim 1, wherein the control means activates the power drive means upon detection by the snoring noise detecting means of a sequence of snoring noises consisting of a snoring noise at a noise level higher than a predetermined upper threshold level which has persisted for a time duration within a first predetermined time range, immediately followed by a snoring noise at a noise level lower than a predetermined lower threshold level of a time duration falling within a second predetermined time range, and immediately followed by a snoring noise at a noise level higher than said predetermined upper threshold level of a time duration falling within said first predetermined time range.

9. A pillow for controlling snoring of a sleeping person comprising:

a stationary base;

a cover rotatably secured to said base for supporting the head of a person, said cover being rotatable about a substantially horizontal axis;

power drive means mounted on said base for rotating said cover;

snoring detecting means for detecting a snoring noise generated by said person; and control means operatively connected to said snoring detecting means and said power drive means for sequentially and periodically activating said power drive means for a predetermined time period upon detection of a snoring noise by said snoring noise detecting means whereby said cover is sequentially periodically rotated for said predetermined period until said snoring detecting means fails to detect a snoring noise, said snoring detecting means effective to maintain said cover stationary when said snoring detecting means fails to detect a snoring noise.

10. The pillow according to claim 9 wherein said control means activates said power drive means only if cyclically occurring snoring noises are detected by said snoring detecting means.

11. The pillow according to claim 10 wherein said control means activates said power drive means only if said cyclically occurring snoring noises occur with a predetermined frequency range.

12. The pillow according to claim 10 wherein said control means activates said power drive means only if said snoring noise exceeds a predetermined threshold amplitude level.

13. The pillow according to claim 10 wherein said control means activates said power drive means only during the occurrence of snoring noise louder than a predetermined threshold amplitude level.

14. A pillow as defined in claim 9 wherein said horizontal axis is parallel to the spine of said person.

15. A pillow as defined in claim 9 wherein said horizontal axis is perpendicular to the spine of said person.

* * * * *

UNITED STATES PATENT AND TRADEMARK OFFICE
CERTIFICATE OF CORRECTION

PATENT NO. : 4,941,478

DATED : July 17, 1990

INVENTOR(S) : Shohei Takeuchi et al

It is certified that error appears in the above-identified patent and that said Letters Patent is hereby corrected as shown below:

Claim 1, Col. 7, line 2, after "rotation" insert --for movement between two end positions which define an angle of rotation--;

Claim 1, Col. 7, line 4, delete "a reciprocating rotational motion" and insert therefor --pivoting movement--;

Claim 1, Col. 7, line 5, after "cover" insert --through said angle of rotation--;

Claim 1, Col. 7, line 12, after "means" insert --, said power drive means causing said cover to rotate through an incremental angle, wherein said angle of rotation divided by said incremental angle is not a whole number,--

Claim 8, Col. 8, line 6, after "level" insert --and--;

Claim 9, Col. 8, line 14, after "axis" insert --for movement between two end positions which define an angle of rotation--;

Claim 9, Col. 8, line 26, after "period" insert --through an incremental angle, wherein said angle of rotation divided by said incremental angle is not a whole number,--.

Signed and Sealed this

Sixteenth Day of July, 1991

Attest:

HARRY F. MANBECK, JR.

Attesting Officer

Commissioner of Patents and Trademarks